(12) United States Patent
Feng

(10) Patent No.: US 9,188,516 B2
(45) Date of Patent: Nov. 17, 2015

(54) DEVICE FOR STAINING SUSPENDED CELLS

(71) Applicant: WUHAN CELL MARKER & MACHINE TECH CO., LTD., Hubei (CN)

(72) Inventor: Jiangnan Feng, Hubei (CN)

(73) Assignee: Wuhan Cell Marker & Machine Tech Co., Ltd., Hubei (CN)

( * ) Notice: Subject to any disclaimer, the term of this patent is extended or adjusted under 35 U.S.C. 154(b) by 0 days.

(21) Appl. No.: 14/352,762

(22) PCT Filed: Oct. 8, 2012

(86) PCT No.: PCT/CN2012/082544
§ 371 (c)(1),
(2) Date: Apr. 18, 2014

(87) PCT Pub. No.: WO2013/056620
PCT Pub. Date: Apr. 25, 2013

(65) Prior Publication Data
US 2014/0335604 A1    Nov. 13, 2014

(30) Foreign Application Priority Data

Oct. 19, 2011   (CN) .......................... 2011 1 0317001
Oct. 19, 2011   (CN) ...................... 2011 2 0397714 U

(51) Int. Cl.
*A61B 10/00*    (2006.01)
*G01N 1/31*     (2006.01)
*G01N 1/40*     (2006.01)

(52) U.S. Cl.
CPC . *G01N 1/31* (2013.01); *G01N 1/405* (2013.01)

(58) Field of Classification Search
CPC ....................................................... G01N 30/02
See application file for complete search history.

(56) References Cited

U.S. PATENT DOCUMENTS 4,971,688 A * 11/1990 Francois et al. ................. 210/94

FOREIGN PATENT DOCUMENTS

| CN | 1755348   | 5/2006 |
|----|-----------|--------|
| CN | 102042924 | 4/2011 |
| CN | 202305300 | 4/2012 |
| EP | 1219963   | 3/2002 |

* cited by examiner

*Primary Examiner* — Jyoti Nagpaul
(74) *Attorney, Agent, or Firm* — Duane Morris LLP

(57) ABSTRACT

A device for staining suspended cells composed of a cannula (1), a pushrod (2), a plunger sealing pad (3), and a capture membrane (4), wherein the plunger sealing pad (3) is located at an upper part within the cavity of the cannula (1), the capture membrane (4) is located at a lower part within the cavity of the cannula (1), and an opening (5) above the membrane and an opening (6) below the membrane are formed on the wall of the cannula (1) respectively. The device is for use in staining suspended cells, is capable of effectively overcoming the drawbacks in current existing methods for staining cells, such as high failure rates, low accuracy and repeatability, and being very time-consuming, etc., and has advantages such as high success rates, good accuracy and repeatability, and not being time-consuming, etc.

7 Claims, 4 Drawing Sheets

| Samples | Observations by fluorescence microscope (fluorescence/normal light) |
|---|---|
| Negative control: FITC-marked rabbit anti-rat IgG antibody at first time | |
| Negative control: FITC-marked rabbit anti-rat IgG antibody at second time | |
| Negative control FITC-marked goat anti-rabbit IgG antibody at first time | |
| Negative control FITC-marked goat anti-rabbit IgG antibody at second time | |
| FITC-marked anti-GAPDH at first time | |
| FITC-marked anti-GAPDH at second time | |

FIG.3

DEVICE FOR STAINING SUSPENDED CELLS

TECHNICAL FIELD

The present invention belongs to the field of immunological technology and biological technology, related to cell staining technology, particularly to a device for staining suspended cells.

BACKGROUND ART

Cytological detection is the most commonly used technology of cell biology. The immunological staining detection method for suspended cells often uses the centrifugal technology to wash cells. The steps of the method include: obtaining a single suspended cell; fixing the cell or not; adding antibodies (or other substances can combine to the cell makers); washing off the unbonded antibodies by centrifugation; adding chromogenic substances; washing off the chromogenic substances by centrifugation; detecting staining conditions. Various detection modes and methods based on different antibodies or anti-antibodies basically repeat the operation steps described above thereby completing cell immunological staining and finally detecting the cell markers.

Conventional cell detection method is barely implementable for the cytomembrane markers detection. However, it becomes difficult when it comes to detection of intracellular markers such as cytoplasm and nucleus markers since the detection requires cytomembrane opening. Once the cytomembrane is opened, the osmotic pressure of cell will be changed thereby recovering cells by centrifugation beding difficult. Further, when the unbonded antibodies being washed of post cell staining, cells can not be tightly compressed to the bottom of the tube after centrifugation due to the change of cell osmotic pressure, thereby cells being removed during the supernatant removal. In most conditions, most cells are lost after the cell staining step is completed, therefore, the experimental results are incorrect or it is hard to complete the experiments. Hence, the immunological staining operation on suspended cells based on centrifugation is very difficult, which costs much time and effort but does not guarantee the result. Cell marker detection becomes more and more widely applied. The difficult operation of cell staining methods seriously blocks the applications of flow cytometer and other cell detection devices.

SUMMARY

The object of the present invention is to provide a device for staining suspended cells, to overcome the defect of the current cytology immunology detection using centrifugation to wash cells, thereby the immune response of suspended cells being quickly operated and completed. The device allows the immune response of suspended cells to be implemented and is featured by high accuracy, good repeatability, strong objectivity and convenient operation.

The specific embodiment to carry out the present invention is:

The device for staining suspended cell provided by the present invention composed of a cannula 1, a pushrod 2, a plunger sealing pad 3 and a capture membrane 4, wherein the cannula 1 is of a hollow cylindrical tubular structure, the plunger sealing pad 3 is of a circular plate structure locating at an upper part within the cavity of the cannula 1, the periphery of which seal fit the inner wall of tubular cavity of the cannula 1 in slidable pattern; wherein the pushrod 2 is of a long rod structure, the front end of which is connected to the top of the plunger sealing pad 3 and forms in one with the plunger sealing pad 3. The capture membrane 4 is located at a lower part within the cavity of the cannula 1, dividing the internal cavity of the cannula 1 into two parts, the cavity above membrane and the cavity below membrane. An opening 5 above the membrane provided for injecting and discharging solution is disposed on the wall of the cannula 1 above the capture membrane 4 where is close to the capture membrane 4. An opening 6 below the membrane provided for injecting and discharging solution is disposed on the wall of the cannula 1 below the capture membrane 4.

The opening 6 below membrane can be disposed either on the lateral wall of the cannula 1 below the capture membrane 4, or on the bottom wall of the cannula 1 below the capture membrane 4; a valve 8 and a valve 9 can be disposed on the opening 5 above membrane and the opening 6 below membrane, wherein the disposed valves may be a single-port valve or a multi-port valve; a pushrod handle 7 can be disposed on the back end of the pushrod 2 to facilitate the operator to hold; the capture membrane 4 can be made of a nylon membrane or a ceramic membrane, used to capture relatively large substances such as cells or subcellular structures and allow relatively small substances such as antibodies to pass through. The passable aperture is 0.1 µm to 50 µm wide, preferably 0.45 µm; The cannula 1, the pushrod 2 and the pushrod handle 7 can be made of plastic or stainless steel, and the plunger sealing pad (3) can be made of rubber.

A plurality of the device for staining suspended cells provided by the present invention can be used in combinations to form combined device for staining suspended cells so as to simultaneously stain more cells. Such combined device for staining suspended cells provided by the present invention comprise of two or more parallelly arranged abovementioned devices for staining suspended cells and a communicating pipe 10 constituted by a hollow tubular structure. The opening 6 below the membrane of each device for staining suspended cells is connected to the communicating pipe 10. Communicating pipe openings 11 provided for injecting and discharging solution are disposed on the both ends of the communicating pipe 10. Valves can be disposed on the communicating pipe openings 11 on the both ends of the communicating pipe 10. A shunting joint 12 can be disposed between a communicating pipe opening on one end of the communicating pipe 10 and the valve disposed on the communicating pipe opening.

The device of the present invention is used for staining suspended cells, wherein pressure is employed to pass antibodies and liquid to be separated through the capture membrane 4 in the cell washing process, while cells and subcellular structures are captured by the capture membrane 4, thereby achieving the washing and separating process for cells and various staining substances. The capture membrane 4 can capture relatively larger substances such as cells and subcellular structures and allow relatively smaller substances like antibodies to pass through.

The pushrod 2 and the plunger sealing pad 3 are integrated in structure, which can be controlled by manual operation or mechanical electro-motion to perform piston motion in the cannula 1. The plunger sealing pad 3 seal fit the cannula 1. When the pushrod 2 and the plunger sealing pad 3 move in the direction to membrane, liquid above the capture membrane 4 can be pressed through but the relatively larger substances such as cells and subcellular structures can not pass through the membrane and thus be captured.

Two openings are disposed on the cannula 1 for injecting and discharging solution, namely the opening 5 above the membrane or the opening 6 below the membrane. The opening 5 above the membrane or the opening 6 below the membrane can be connected to valves or connected to shunting joints before connected to valves, to facilitate the injection and discharge of different solutions. Various forms of valves can be selected such as multi-channel or electric valves with which automation can be achieved. On the valves, various forms of pumps can be connected.

The device for staining suspended cells provided by the present invention can be operated in the following method for usage:

1. Adding cells: inject suspended cells fixed in 70% ethanol which is to be stained in the cavity above the capture membrane 4 in the cannula 1 via the opening above the membrane 5. The injection can be made by pressure pump, peristaltic pump, and piston pump or by syringe, etc. close the opening above membrane 5 after injection.

2. Washing cells:

a. push the pushrod 2 down so that the plunger sealing pad 3 is pressed to move in the direction to the capture membrane 4, thereby making the ethanol in the cavity above the capture membrane 4 be discharged via the opening below the membrane 6 after passing through the capture membrane 4. Close the opening below the membrane 6 after the ethanol is discharged, while the cells to be stained are captured on the capture membrane 4;

b. inject the washing solution by a peristaltic pump via the opening 6 below the membrane, simultaneously make the pushrod 2 and the plunger sealing pad 3 move in the direction away from the capture membrane 4, and for the moment the washing solution is injected in the cavity above the capture membrane 4 through the capture membrane 4. Washing solutions are different in different staining methods, and different washing solutions can be used in the same staining method. For example immunofluorescence staining experiments usually use Dulbecco's Hanks Balanced Salt Solution (without $Ca^{2+}$ and $Mg^{2+}$) or PBS solution, and enzyme immunostaining uses PBST solution;

c. press the pushrod 2 and the plunger sealing pad 3 to move in the direction to the capture membrane 4, thereby making the washing solution in the cavity above the capture membrane 4 be discharged via the opening 6 below the membrane after it passes through the capture membrane 4, while the cells subjected to washing are captured on the capture membrane 4;

Repeat the sub-step c in the step 2 described above for 7-8 times.

3. Adding staining substances: inject staining substances such as antibodies, anti-antibodies, enzymes, enzyme substrates, biological dyes and chemical dyes, etc., to the cavity above the capture membrane 4 in the cannula 1 via the opening 5 above the membrane, wherein a pressure pump can be used to add staining substances via the opening 5 above membrane. Close the opening 5 above membrane after injection and leave for an appropriate time to facilitate immune response or staining.

4. Washing cells: the operation is the same as the sub-step c in the step 2 above. Repeat the sub-step c in the step 2 described above for 4-6 times to wash off unbonded antibodies or staining substances.

5. Collect cells post staining: open the opening 5 above the membrane. Washing solution is injected via the opening 6 below the membrane by a peristaltic pump and simultaneously the effluent containing the stained cells is collected from the opening 5 below the membrane. At this time cell staining is completed.

The present invention is applicable to the field of medical and biological technology. Cells are the most important target of research and application in the field of medical and biological technology. Cell staining, particularly immunostaining (e.g., immunofluorescence staining, enzyme immunostaining) is a method commonly used for cell analysis. However, the problem of high failure rate of experiments and detections resulted from operation difficulties in suspended cell staining using the prior art is always pended. The device for staining suspended cells of the present invention overcomes the problem described above. The device of the present invention can effectively guarantee the success of staining suspended cells, while staining with conventional centrifugation method often ends up with failure due to cell loss. Cell staining of the device of the present invention has high accuracy, good repeatability and strong objectivity, which is not affected by artificial factors, and greatly shortens the required staining time. The operating time of conventional centrifugation method is fairly long that a standard cell antibody, anti-antibody staining process requires 3 hours to 4 hours, while the device of the present invention just requires 1.5 hours.

The advantage effect of the present invention: (1) Successful cell immunostaining is guaranteed: after cells are fixed, since cytomembranes are broken through, the cells can not be tightly compressed to the bottom of the centrifugal tube by centrifugal force under the conventional centrifugation operation, which make the cells simultaneously removed during supernatant removal. Repeated cell washing causes great cell loss and the experiment end up with failure. (2) The accuracy, repeatability and objectivity of the immunostaining or other staining is enhanced: the present invention can achieve automatic operation, overcome the experimental deviation generated from operations of different people, and make suspended cell staining achieve automation, standardization and acceleration. (3) Time consumption and equipment requirement are smaller: in immunostaining by conventional centrifugation method, high rotational speed and long-time centrifugation are needed as cells can hardly be tightly compressed to the bottom of the centrifugal tube by centrifugal force, therefore, the total immune response takes longer time. However, the present device can largely save time and reduce the requirements for the centrifugal machine.

Hereinafter the present invention is further illustrated through specific examples. The following examples do not limit the scope of the present invention.

Figure 1:
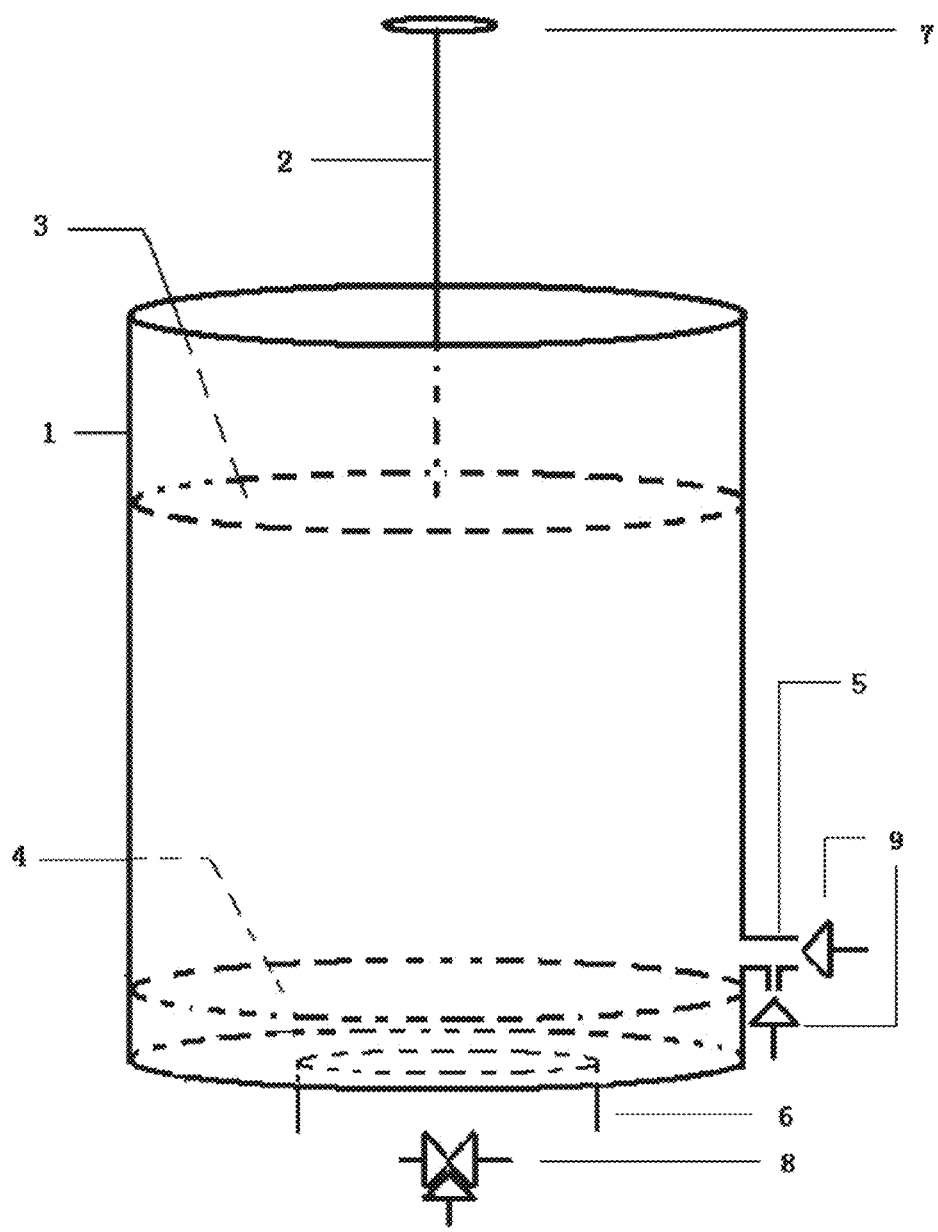
FIG. 1 is the structure diagram of one example for the device for staining suspended cells of the present invention.

The parts indicated by the numbers in FIG. 1 are:

1: Cannula

2: Pushrod

3: Plunger sealing pad

4: Capture membrane

5: Opening above the membrane

6: Opening below the membrane

7: Pushrod handle

8: Valve on the opening below the membrane

9: Valve on the opening above the membrane

Figure 2:
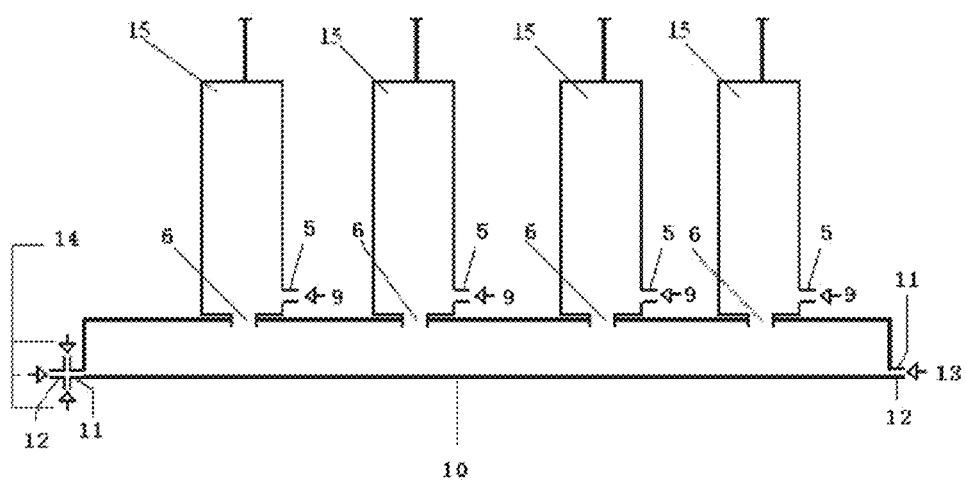

FIG. 2 is the structure diagram of the combined device for staining suspended cells of the example 2.

The parts indicated by the numbers in FIG. 2 are:

5: Opening above the membrane

6: Opening below the membrane

9: Valve the opening above the membrane

10: Communicating pipe

11: Communicating pipe opening
12: Shunting joint
13, 14: Valves
15: Device for staining suspended cells FIG. 3 is the cellular fluorescence staining result observed by microscope in example 3.

Figure 4:
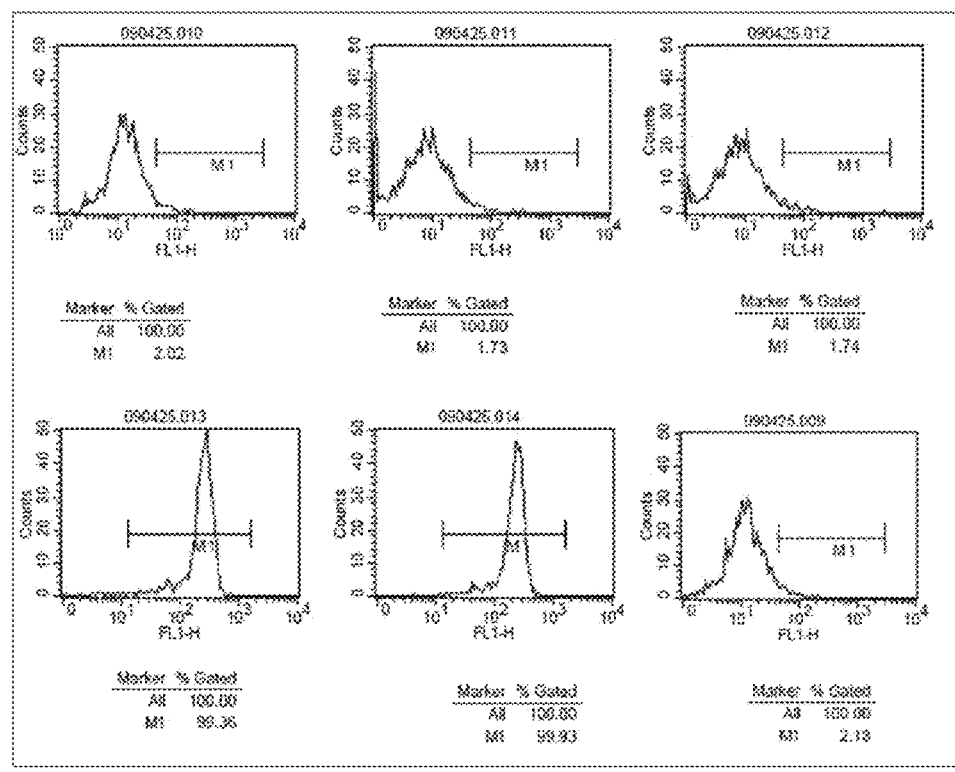

FIG. 4 is the fluorescence result of stained cells determined by flow cytometer in example 3.

DETAILED DESCRIPTION

Example 1

FIG. 1 is the structure of an embodiment of the device for staining suspended cells of the present invention. The device for staining suspended cells is composed of a cannula 1, a pushrod 2, a plunger sealing pad 3 and a capture membrane 4, wherein the cannula 1 is made of plastic or stainless steel and is of a hollow cylindrical tubular structure, wherein the plunger sealing pad 3 is of a circular plate structure locating at an upper part within the cavity of the cannula 1. The periphery of the plunger sealing pad 3 seal fit the inner wall of tubular cavity of the cannula 1 in a slidable pattern. The pushrod 2 is of a long rod structure, the front end of which is connected to the top of the plunger sealing pad 3 and integrate with the plunger sealing pad 3 into one body. A pushrod handle 7 can be disposed on the back end of the pushrod 2 to facilitate the operator to hold. The capture membrane 4 is located at a lower part within the cavity of the cannula 1. An opening 5 above the membrane provided for injecting and discharging solution is disposed on the wall of the cannula 1 above the capture membrane 4, where is close to the capture membrane 4. An opening 6 below the membrane provided for injecting and discharging solution is disposed on the wall of the cannula 1 below the capture membrane 4. A valve 9 is disposed on the opening 5 above the membrane, and a valve 8 is disposed on the opening 6 below the membrane, wherein the valve 8 is formed by a three-port valve; the capture membrane 4 is a nylon membrane or a ceramic membrane, able to capture relatively large substances like cells or subcellular structures and allow relatively small substances like antibodies to pass through. The capture membrane 4 in use is the nylon membrane with a passable aperture of 0.45 μm manufactured by the Pirce Company. The valve 8 in use is a luer valve, specifically a medical three-port valve produced by Jiyou Plastic Technology Development Co., Ltd. The valve 9 uses a large-sized detaining needle as a three-port valve. The cannula (1) is made of plastic or stainless steel. The height of the cannula 1 is 10 centimeters, the inner diameter is 1 centimeter and the thickness of the wall of the cannula 1 is 0.2 centimeter. The pushrod 2 is made of plastic or stainless steel. The plunger sealing pad 3 is made of rubber.

Example 2

The combined device for staining suspended cells, namely a combined utilization of the devices for staining suspended cells.

The device for staining suspended cells provided by the present invention can be used in combinations. Two or more devices for staining cells can be used in combination, so as to simultaneously treat more cells, that is, stain more cells simultaneously.

FIG. 2 is an embodiment of four devices for staining suspended cells being used in combination. The specific combined mode thereof is: a communicating pipe 10 is disposed below four parallelly arranged devices for staining suspended cells. The openings 6 below the membrane for injecting and discharging solution on the cannula 1 of the four devices for staining suspended cells are connected to the communicating pipe 10. Openings 11 are disposed on the both ends of the communicating pipe 10, wherein a shunting joint 12 is formed on the opening of one end, a valve 14 is disposed on the shunting opening of the shunting joint 12 and a valve 13 is disposed on the opening of the other end. The communicating pipe 10 is of a hollow cylindrical tubular structure, and can be made of materials like rubber, stainless steel and organic glass, etc.

In usage, cells to be stained and staining substances are injected via the opening 5 above the membrane; During cell washing, the washing solution is injected by a pressure pump via the opening 5 above the membrane or an opening on one end of the communicating pipe 10. In the present example, the washing solution is injected via the communicating pipe opening connecting the shunting joint 12. After injected in the inner cavity of the communicating pipe 10, the washing solution flows into the cavity of each device for staining suspended cells via opening 6 below the membrane of each device for staining suspended cells. While injecting the washing solution via the communicating pipe opening connected to the shunting joint 12, the pushrod 2 and the plunger sealing pad 3 are made to move in the direction away from the capture membrane 4, thereby making the injected washing solution pass through the capture membrane and flow into the cavity above the capture membrane 4 of the cannula 1; after the washing solution is injected, the communicating pipe opening containing the shunting joint 12 is closed. In the present example, it is achieved by controlling the valve 14 on the shunting joint 12. The washing solution is discharged via the opening on the other end of the communicating pipe 10. When the stained cells are collected, the pushrod 2 ad the plunger sealing pad 3 are moved in the direction to the capture membrane 4 and the plunger sealing pad 3 is stopped where is closed to the capture membrane 4. The opening 5 above the membrane is opened, and the solution is injected by a pressure pump via the opening on one end of the communicating pipe 10. For this moment, the opening on the other end of the communicating pipe is switched in closed state. Effluent out of the opening 5 above the membrane is collected, which contains the stained cells, that is, the stained cells are collected via the opening 5 above the membrane.

Example 3

The device for staining suspended cells prepared in the example 1 is used to conduct the immunofluorescence cell staining experiment.

Experimental Steps: See FIG. 1

1. Adding cells: the valve 9 is opened. Suspended cells fixed in 70% ethanol which is to be stained are injected in the cavity above the capture membrane 4 in the cannula 1. After injection, the valve 9 is closed.

2. Washing cells:

a. The valve 8 is opened. The plunger sealing pad is pressed to move in the direction to the capture membrane 4, thereby making the ethanol in the cavity above the capture membrane 4 passing through the capture membrane 4 before it goes through the opening 6 below the membrane for injecting and discharging solution and is discharged by one port among the three-port valve forming the valve 8. After ethanol is discharged, the valve port is closed. Meanwhile, the cells to be stained are captured on the capture membrane 4;

b. The washing solution is injected by a peristaltic pump via another port among the three-port valve forming the valve 8. At the same time the plunger sealing pad is forced to move in the direction away from the capture membrane 4, while the washing solution is injected in the cavity above the capture membrane 4 of the cannula 1 through the capture membrane 4. The port for injecting washing solution among the three-port valve forming the valve 8 is closed, and another port among the three-port valve forming the valve 8 is opened;

c. The plunger sealing pad 3 is pressed to move in the direction to the capture membrane 4, thereby making the washing solution in the cavity above the capture membrane 4 go through the opening below the membrane 6 for injecting and discharging solution and be discharged by the open port among the three-port valve forming the valve 8 after it passes through the capture membrane 4. At this time, the cells subjected to washing are captured on the capture membrane 4;

The sub-step c in step 2 mentioned above is repeated for 8 times.

3. Adding FITC-marked antibody: the valve 9 is opened. 200 ul of FITC-marked antibody solution is injected in the cavity above the capture membrane in the cannula 1. After injection the valve 9 is closed. It is placed under room temperature for 30 minutes.

4. Washing cells: same with the sub-step c in step 2 mentioned above; repeat for 5 times.

5. Collecting cells post staining: Open the valve 9. The washing solution is injected via one port among the three-port valve forming the valve 8 by a peristaltic pump. At the same time the effluent containing the stained cells is collected from the valve 9. At this time cell staining is completed.

Example 4

Immunofluorescence Staining Experiment

I. Experimental Materials

1. PNC-1 cell line cells: cultured PNC—1 cell line cells were washed for 3 times after digestion by trypsin. Anhydrous ethyl alcohol was added to a concentration of 70%, left at room temperature for 20 minutes.

2. FITC-marked rabbit anti-human GAPDH antibody, irrelevant antibody: FITC-marked rabbit anti-rat IgG antibody, FITC-marked goat anti-rabbit IgG antibody: are products of Wuhan Genesil Biotechnology Co., Ltd.

The dilution titer is 1:200.

3. Anhydrous ethyl alcohol: Shanghai Sinopharm Chemical Reagent Co., Ltd

4. Washing solution: 0.15 Mol PBS solution, prepared by conventional method.

II. Experimental Method

Cell staining was conducted by the method described in example 3, and the stained cells were obtained.

III. Experimental Results:

The cellular fluorescence staining results were tested on the obtained stained cells using flow cytometer and fluorescence microscope. The results tested by both methods both demonstrate that the experiment is successful. The staining result observed by fluorescence microscope is shown in FIG. 3. The result of cells stained by fluorescence is shown in table 1, FIG. 4.

TABLE 1

The cellular fluorescence result determined by flow cytometer

| Sample | FACS positive rate |
|---|---|
| Negative control: FITC-marked rabbit anti-rat IgG antibody at first time | 2.02 |
| Negative control: FITC-marked rabbit anti-rat IgG antibody at second time | 1.73 |
| Negative control: FITC-marked goat anti-rabbit IgG antibody at first time | 1.74 |
| FITC-marked anti-GAPDH at first time | 99.36 |
| FITC-marked anti-GAPDH at second time | 99.93 |
| Negative control: FITC-marked goat anti-rabbit IgG antibody at second time | 2.13 |

Success are made with all the staining samples.

EXPERIMENTAL CONCLUSION

Dealing the fixed suspended cells by the device for staining suspended cells can stain the FITC-marked GAPDH antibody to the PNC-1 cells. The FITC marked control antibodies were not stained. The staining process is convenient and rapid. In the staining results, the nonspecific background of cellular fluorescence is low and the positive rate is high.

The invention claimed is:

1. A device for staining suspended cells, which is composed of a cannula (1), a pushrod (2), a plunger sealing pad (3) and a capture membrane (4), wherein the cannula 1 is of a hollow cylindrical tubular structure, and the plunger sealing pad (3) is of a circular plate structure, locating at an upper part within the cavity of the cannula (1); The periphery of the plunger sealing pad 3 seal fit the inner wall of tubular cavity of the cannula 1 in slidable pattern; The pushrod (2) is of a long rod structure, the front end of which is connected to the top of the plunger sealing pad (3) and integrate with the plunger sealing pad (3) into one body; The capture membrane (4) is located at a lower part within the cavity of the cannula (1), dividing the internal cavity of the cannula (1) into two parts, the cavity above membrane and the cavity below membrane; An opening (5) above the membrane provided for injecting and discharging solution is disposed on the wall of the cannula (1) above the capture membrane (4), where is close to the capture membrane (4); An opening (6) below the membrane provided for injecting and discharging solution is disposed on the wall of the cannula (1) below the capture membrane (4);

wherein valves (8, 9) are disposed on the opening (5) above the membrane and/or the opening (6) below the membrane, and the valve is a multi-port valve;

wherein the opening (6) below membrane can be disposed either on the lateral wall of the cannula (1) below the capture membrane (4), or on the bottom wall of the cannula (1) below the capture membrane (4); and wherein the capture membrane (4) can be made of a nylon membrane or a ceramic membrane and passable aperture of the capture membrane (4) is 0.1 μm to 50 μm.

2. The device for staining suspended cells according to claim 1, wherein a pushrod handle (7) can be disposed on the back end of the pushrod (2) to facilitate the operator to hold.

3. The device for staining suspended cells according to claim 1, wherein passable aperture of the capture membrane (4) is 0.45 μm.

4. The device for staining suspended cells according to claim 1, wherein the cannula (1), the pushrod (2) can be made of plastic or stainless steel; the pushrod (2) and the pushrod handle (7) can be made of plastic or stainless steel; the plunger sealing pad (3) can be made of rubber.

5. A combined device for staining suspended cells, which is composed of two or more parallelly arranged devices for staining suspended cells according to any of claim 4 and a communicating pipe (10) constituted by a hollow tubular structure; the opening (6) below the membrane of each device for staining suspended cells is connected to the communicating pipe (10); communicating pipe openings (11) provided for injecting and discharging solution are disposed on the both ends of the communicating pipe 10.

6. The combined device for staining suspended cells according to claim 5, wherein valves are disposed on the communicating pipe openings (11) on both ends of the communicating pipe (10).

7. The combined device for staining suspended cells according to claim 5, wherein a shunting joint (12) is disposed on the opening of one end of the communicating pipe (10), wherein a valve (14) is disposed on the shunting opening of the shunting joint (12); a valve (13) is disposed on the opening of the other end of the communicating pipe (10).

* * * * *